United States Patent
Hosoya et al.

(10) Patent No.: US 6,712,054 B2
(45) Date of Patent: Mar. 30, 2004

(54) DEVICE AND METHOD FOR MEASURING ELEMENT TEMPERATURE OF AIR-FUEL RATIO SENSOR, AND DEVICE AND METHOD FOR CONTROLLING HEATER OF AIR-FUEL RATIO SENSOR

(75) Inventors: Hajime Hosoya, Atsugi (JP); Koji Takahashi, Atsugi (JP); Shigeo Ohkuma, Atsugi (JP)

(73) Assignee: Unisia Jecs Corporation, Kanagawa-ken (JP)

( * ) Notice: Subject to any disclaimer, the term of this patent is extended or adjusted under 35 U.S.C. 154(b) by 0 days.

(21) Appl. No.: 09/853,872

(22) Filed: May 14, 2001

(65) Prior Publication Data

US 2002/0008100 A1 Jan. 24, 2002

(30) Foreign Application Priority Data

May 17, 2000 (JP) .......... 2000-144427
Jun. 29, 2000 (JP) .......... 2000-197020

(51) Int. Cl.$^7$ .............................. F02D 45/00
(52) U.S. Cl. ............ 123/697; 73/23.32; 204/406; 204/425
(58) Field of Search .......... 123/697; 73/23.32; 204/406, 425

(56) References Cited

U.S. PATENT DOCUMENTS

| | | | | | |
|---|---|---|---|---|---|
| 4,626,338 | A | * | 12/1986 | Kondo et al. | 204/406 |
| 5,148,795 | A | * | 9/1992 | Nagai et al. | 123/697 |
| 5,405,521 | A | * | 4/1995 | Nakamori et al. | 204/425 |
| 5,454,259 | A | * | 10/1995 | Ishii et al. | 73/118.1 |
| 5,671,721 | A | * | 9/1997 | Aoki | 123/688 |
| 5,758,310 | A | * | 5/1998 | Kato | 701/109 |
| 5,787,866 | A | * | 8/1998 | Sugiyama et al. | 123/672 |
| 5,833,836 | A | * | 11/1998 | Takami et al. | 205/785 |
| 5,836,292 | A | * | 11/1998 | Aoki | 123/697 |
| 5,852,228 | A | * | 12/1998 | Yamashita et al. | 73/23.32 |
| 5,993,641 | A | * | 11/1999 | Okazaki et al. | 205/784.5 |
| 6,083,369 | A | * | 7/2000 | Tanigawa | 204/424 |
| 6,120,677 | A | * | 9/2000 | Yamada et al. | 205/785 |

FOREIGN PATENT DOCUMENTS

| | | |
|---|---|---|
| JP | 61-122556 | 6/1986 |
| JP | 08-278279 | 10/1996 |
| JP | 11-344466 | 12/1999 |

* cited by examiner

*Primary Examiner*—Willis R. Wolfe
*Assistant Examiner*—Johnny H. Hoang
(74) *Attorney, Agent, or Firm*—McDermott, Will & Emery

(57) ABSTRACT

A device according to the present invention is provided with element temperature measurement voltage application circuit for temporarily applying a predetermined voltage for element temperature measurement to a sensor element of an air-fuel ratio sensor equipped to an exhaust system of an internal combustion engine, first sensor output reading circuit for reading in a sensor output just before applied with the voltage, and second sensor output reading circuit for reading in a sensor output being applied with the voltage, wherein the element temperature of the air-fuel ratio sensor is estimated based on the sensor output just before applied with the voltage and the sensor output being applied with the voltage. Further, during internal resistance measurement of the sensor element of the air-fuel ratio sensor equipped to the exhaust system of the internal combustion engine, a voltage applied to the heater for heating the sensor element is maintained to be constant.

9 Claims, 14 Drawing Sheets

DEVICE AND METHOD FOR MEASURING ELEMENT TEMPERATURE OF AIR-FUEL RATIO SENSOR, AND DEVICE AND METHOD FOR CONTROLLING HEATER OF AIR-FUEL RATIO SENSOR

FIELD OF THE INVENTION

The present invention relates to a technique for measuring the element temperature of an air-fuel ratio sensor (including an oxygen sensor) equipped to an exhaust system of an internal combustion engine and utilized for controlling an air-fuel ratio of the engine, and to a technique for controlling a heater for heating a sensor element equipped to the air-fuel ratio sensor based on the measured element temperature.

DESCRIPTION OF THE RELATED ART

Heretofore, there has been known an air-fuel ratio control device of an internal combustion engine for detecting an actual air-fuel ratio of the engine based on the oxygen concentration and the like in the exhaust using an air-fuel ratio sensor, and performing a feedback control of fuel supply quantity to the engine so that the actual air-fuel ratio reaches a target air-fuel ratio.

In order to perform the above-mentioned air-fuel ratio feedback control, it is required that the air-fuel ratio sensor is already activated. Since the air-fuel ratio sensor is activated when the element temperature reaches a predetermined activation temperature, the air-fuel ratio sensor is equipped with a heater for heating the sensor element, so as to control the element temperature to the target temperature by controlling the power supply to the heater.

Specifically, the internal resistance of the sensor element is measured, and based on the element temperature estimated from the measured resistance, a power supply amount to the heater is feedback controlled so that the element temperature reaches the target temperature (refer to Japanese Unexamined Patent Publication Nos. 8-278279, 61-122556, 11-344466, etc.).

However, in a case where, for measuring the element temperature of the air-fuel ratio sensor (or the internal resistance of the sensor element related thereto), a predetermined voltage for measuring the element temperature (or for measuring the internal resistance) is applied to the sensor element, to measure the internal resistance based on the sensor output at that time, a voltage for detecting the air-fuel ratio is continuously output from the air-fuel ratio sensor even during internal resistance measurement (during application of measurement voltage). Therefore, if the sensor output is used as it is for measurement of internal resistance, an estimation error of the element temperature becomes too large.

Moreover, in recent years, the sensor element has been miniaturized and the capacity of the heater has been increased for the purposes of activating the sensor element quickly and maintaining the activated state securely, thereby improving the temperature follow-up capability of the sensor element against the power supply to the heater (relatively reducing the heat capacity of the sensor element). Therefore, especially in an air-fuel ratio control device wherein the power supply to the heater is controlled by performing a duty-control of the ON/OFF of the heater power supply, due to this ON/OFF of the heater power supply, the sensor element temperature is fluctuated momentarily and the internal resistance of the element is also fluctuated. This causes an error in the measurement of internal resistance, to lead to the deterioration of estimation accuracy of the element temperature.

Such deterioration of estimation accuracy of the element temperature not only causes the deterioration of the ability to control the element to the target temperature when controlling the power supply to the heater for heating the sensor element, but also causes the increase of the power consumption by the heater. It further causes a bad influence to the feedback control of the air-fuel ratio.

SUMMARY OF THE INVENTION

The present invention has been achieved in view of the above conventional problems and has an object to enable a more accurate measurement of the element temperature in an air-fuel ratio sensor.

Another object of the present invention is to enable an accurate judgment of the activation status of the air-fuel ratio sensor based on the accurately measured element temperature.

Yet another object of the present invention is to control a sensor element to the desired element temperature by controlling a heater for heating the sensor element based on the accurately measured element temperature.

Still another object of the present invention is to improve the accuracy of an air-fuel ratio feedback control based on the above heater control.

In order to achieve the above objects, the present invention is constituted as follows.

When applying a predetermined voltage for measuring the element temperature to the sensor element of the air-fuel ratio sensor, both a sensor output just before applied with the predetermined voltage as well as a sensor output being applied with the predetermined voltage are read in.

Based on both the sensor output just before applied with the predetermined voltage and the sensor output being applied with the voltage, the sensor element temperature is estimated.

With this constitution, since there can be considered an influence of voltage output for air-fuel ratio detection of the air-fuel ratio sensor by the sensor output just before applied with the voltage, the estimation accuracy of the sensor element temperature is improved, thereby enabling an accurate activation judgment and the like of the air-fuel ratio sensor.

Using the sensor output being applied with the predetermined voltage as a basis, and using the sensor output just before applied with the voltage as a correction parameter, the element temperature can be estimated, and further, by computing the internal resistance of the sensor element based on the sensor output, the element temperature can be estimated.

Even further, during internal resistance measurement of the sensor element of the air-fuel ratio sensor, a voltage applied to the heater for heating the sensor element is maintained to be constant.

Thereby, it becomes possible to prevent the fluctuation of sensor element temperature (in other words, the fluctuation of internal resistance of the sensor element), which is caused by the fluctuation of heater application voltage accompanying the control of the heater for heating the sensor element, so that the internal resistance of the sensor element can be measured accurately, and the element temperature can be accurately computed based on the measured internal resistance.

Further, it becomes possible to feedback control the heater for heating the sensor element, based on the accurately detected element temperature, so that the element temperature reaches a target temperature, thereby enabling the sensor element to be controlled to the desired temperature.

The other objects and features of the present invention will become understood from the following description with reference to accompanying drawings.

DETAILED DESCRIPTION OF THE PREFERRED EMBODIMENT

Embodiments of the present invention will now be explained.

Figure 1:
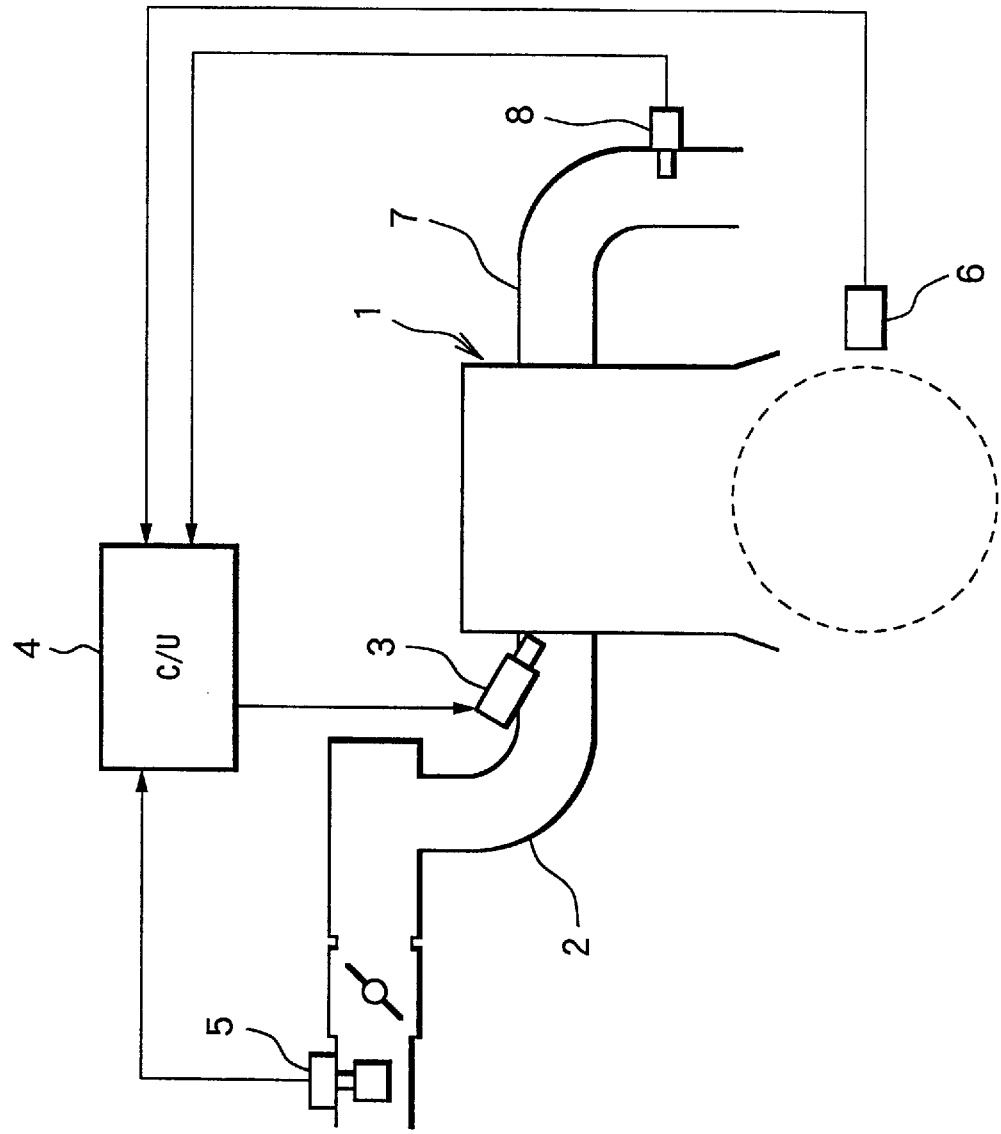
FIG. 1 is a system diagram of an air-fuel ratio feedback control device of an engine showing an embodiment of the present invention.

FIG. 1 is a system diagram showing an air-fuel ratio feedback control device of an internal combustion engine.

The internal combustion engine (hereinafter referred to as engine) 1 is provided with, for each cylinder, a fuel injection valve 3 facing either an intake passage 2 or a combustion chamber. A control unit 4 controls the fuel injection performed by each fuel injection valve 3.

The control unit 4 computes a basic fuel injection quantity $Tp=K \times Qa/Ne$ (wherein K is constant) equivalent to stoichiometric amount of air ($\lambda=1$), from for example an intake air quantity Qa detected based on a signal output from an airflow meter 5 and an engine rotation speed Ne detected based on a signal output from a crank angle sensor 6. The computed basic fuel injection quantity is then corrected by both a target air-fuel ratio $t\lambda$ and an air-fuel ratio feedback correction coefficient < based on a signal output from an air-fuel ratio sensor 8 disposed in an exhaust passage 7, thereby computing a final fuel injection quantity $Ti=Tp \times (1/t\lambda) \times \alpha$. A fuel injection pulse having a pulse width corresponding to the computed fuel injection quantity Ti is output to each fuel injection valve 3 in synchronism with the engine rotation.

Here, the air-fuel ratio sensor 8 is disposed in the exhaust passage 7 for outputting signals corresponding to the oxygen concentration in the exhaust. Based on the signals output from the air-fuel ratio sensor 8, the control unit 4 detects an air-fuel ratio $\lambda$ of the air-fuel mixture supplied to the engine 1, and increasingly/decreasingly sets the air-fuel ratio feedback correction coefficient $\alpha$ using a proportional-plus-integral control and the like, to feedback control the air-fuel ratio $\lambda$ of the air-fuel mixture so that the air-fuel ratio $\lambda$ of the air-fuel mixture reaches the target air-fuel ratio $t\lambda$.

Moreover, the air-fuel ratio sensor 8 is a so-called wide-range air-fuel ratio sensor capable of detecting an air-fuel ratio linearly by varying an output voltage thereof continuously in accordance with the air-fuel ratio, which is equipped with a heater for heating a sensor element.

Figure 2:
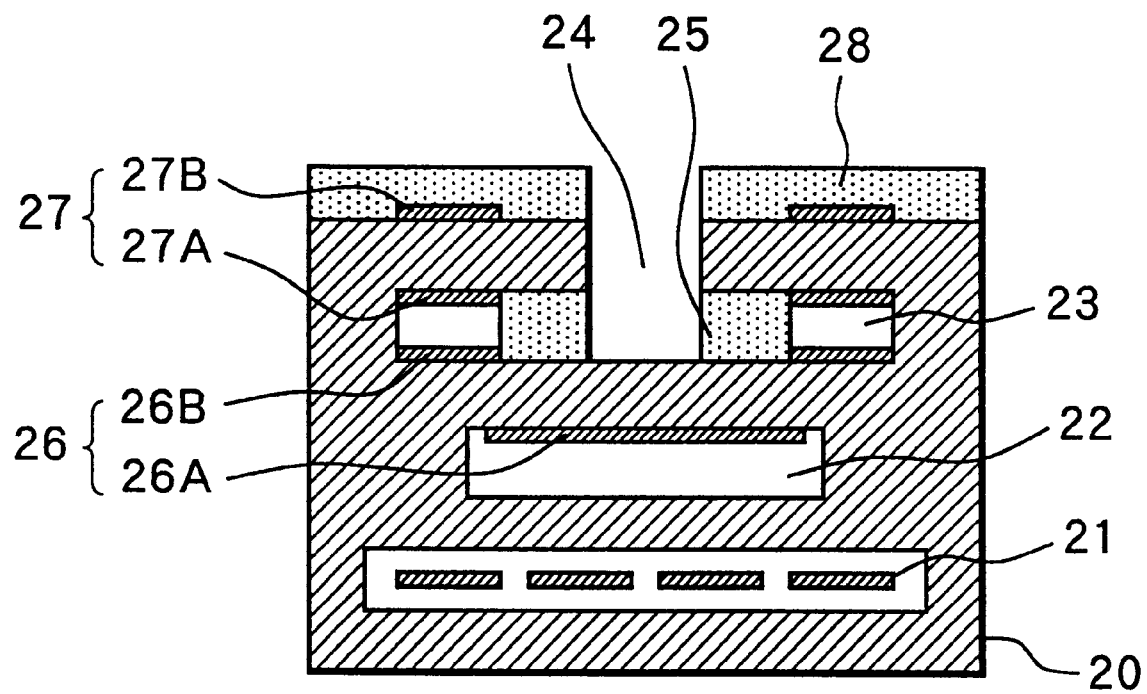
FIG. 2 is a diagram showing the structure of sensor element of the air-fuel ratio sensor.

The structure of the air-fuel ratio sensor 8 is shown in FIG. 2.

In FIG. 2, a sensor element body 20 is formed into porous layers with solid electrolyte material such as zirconia having oxygen ion conductivity. Within the sensor element body 20, there is provided a heater 21, an atmosphere chamber 22, and a gas diffusion chamber 23, from the bottom up in the figure.

The heater 21 heats a sensor element when power is supplied to the heater 21.

The atmosphere chamber 22 is formed so as to communicate with the atmosphere being the reference gas, outside the exhaust passage.

The gas diffusion chamber 23 is formed to communicate with the exhaust through an exhaust introduction hole 24 formed to the upper surface side of the body 20 in the figure, and through a protection layer 25 formed of γ alumina and the like.

A Nernst cell portion 26 is constituted by an electrode 26A formed on the upper wall of the atmosphere chamber 22 and an electrode 26B formed on the lower wall of the gas diffusion chamber 23.

Moreover, a pump cell portion 27 is constituted by an electrode 27A formed on the upper wall of the gas diffusion chamber 23 and an electrode 27B formed on the upper wall of the body 20 and covered by the protection layer 28.

The Nernst cell portion 26 generates a voltage in accordance with an oxygen partial pressure between the Nernst cell portion electrodes 26A and 26B influenced by the oxygen ion concentration (oxygen partial pressure) within the gas diffusion chamber 23. Therefore, by detecting this voltage, it is possible to detect whether the air-fuel ratio is rich or lean relative to the stoichiometric amount of air ($\lambda=1$).

When a predetermined voltage is applied to the pump cell portion 27, the oxygen ion within the gas diffusion chamber 23 moves so that the current flows between the pump cell portion electrodes 27A and 27B. Since the current value (limit current value) Ip flowing between the pump cell portion electrodes 27A and 27B when a predetermined voltage is applied thereto is influenced by the oxygen ion concentration within the gas diffusion chamber 23, by detecting the current value Ip, the air-fuel ratio of the exhaust can be detected.

Figure 3A:
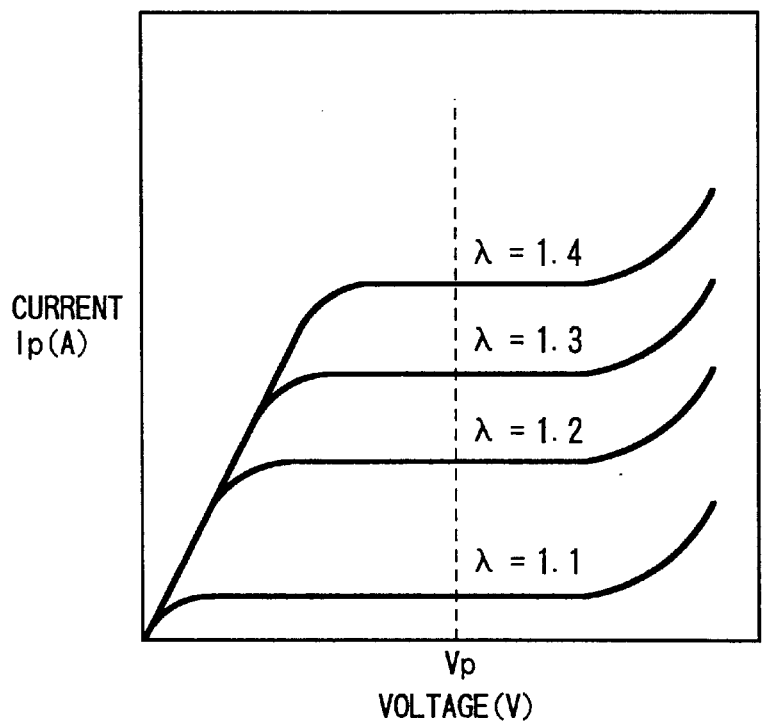
FIGS. 3(a) and 3(b) is a characteristic chart showing the sensor element of the air-fuel ratio sensor.

In other words, as shown in FIG. 3A, since a voltage-current characteristic of the pump cell portion 27 is varied in accordance with the air-fuel ratio $\lambda$, the air-fuel ratio of the exhaust can be detected from the current value Ip when a predetermined voltage Vp is applied to the pump cell portion 27.

Figure 3B:
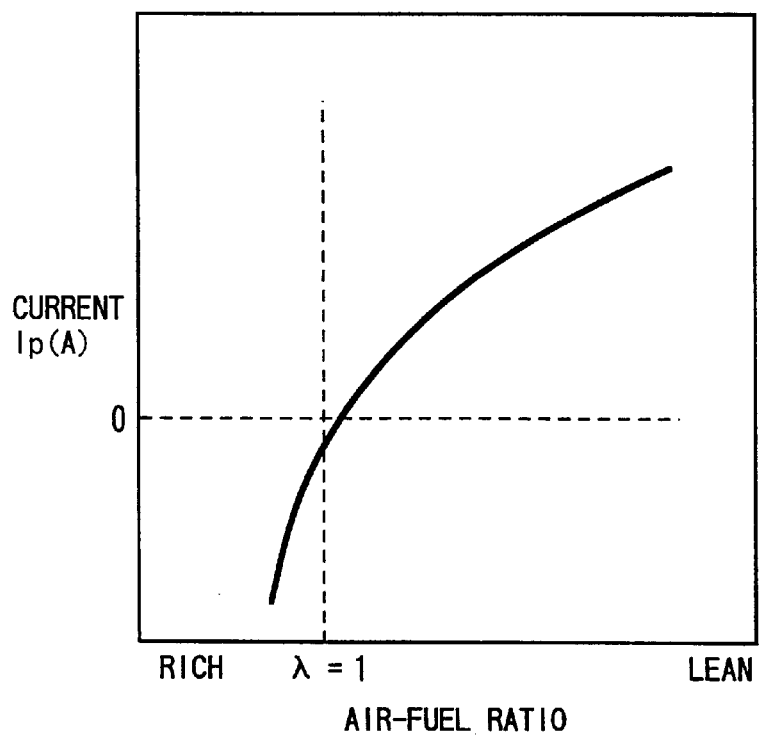

Moreover, based on the lean/rich output by the Nernst cell portion 26, the direction of voltage application to the pump cell portion 27 is reversed, so that in both the lean and rich regions of the air-fuel ratio, a wide range detection of air-fuel ratio λ can be performed based on the current value Ip flowing through the pump cell portion 27, as shown in FIG. 3B.

Figure 4:
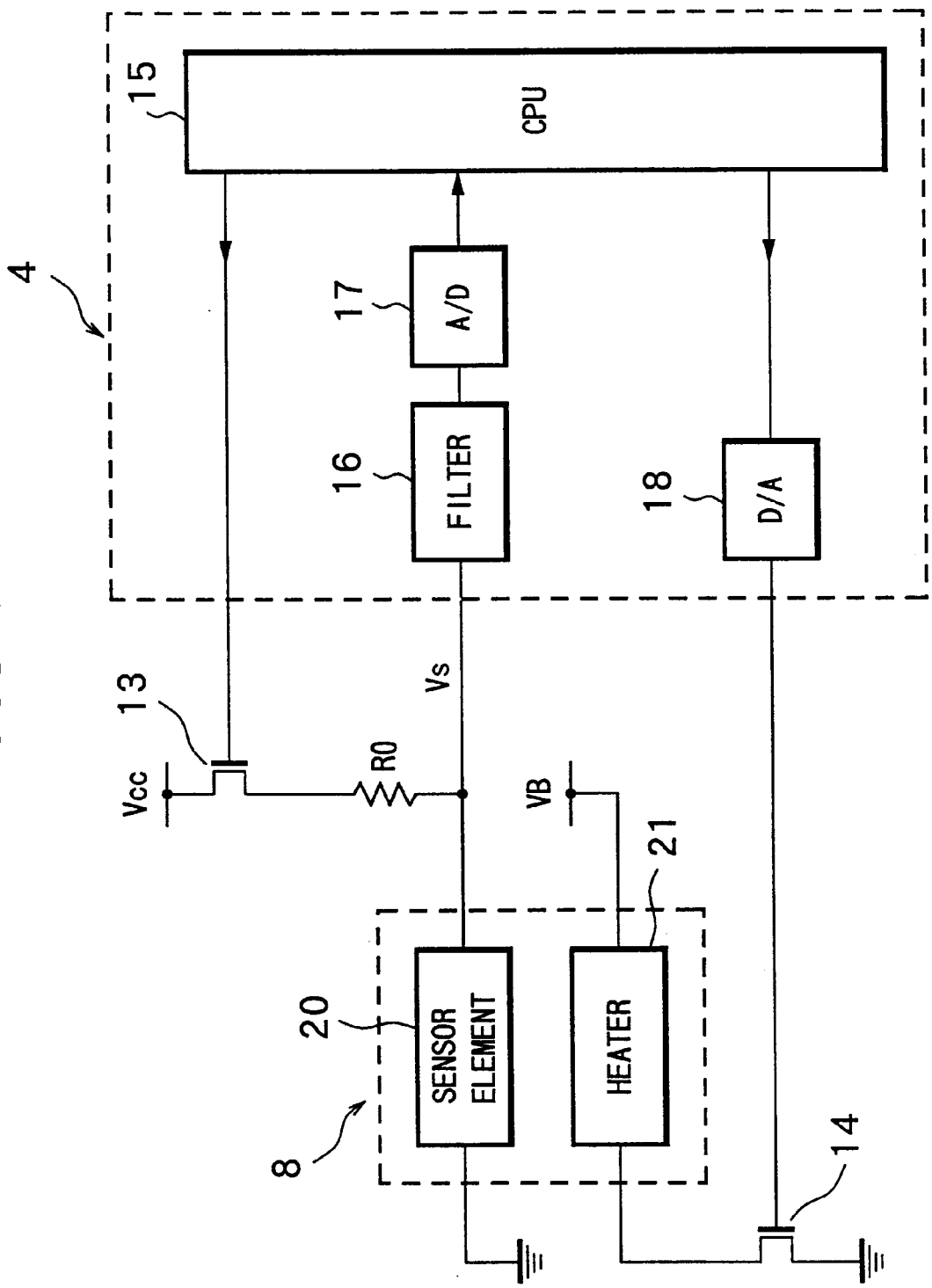
FIG. 4 is a first control circuit diagram for a heater and the sensor element of the air-fuel ratio sensor.

FIG. 4 shows a first control circuit for the sensor element 20 and heater 21 for heating the sensor element in the air-fuel ratio sensor 8.

An output voltage Vs of the sensor element 20 in the air-fuel ratio sensor 8 is varied continuously in accordance with the air-fuel ratio, and this output Vs is input to the control unit 4.

Further, a predetermined voltage Vcc (for example, 5V) for measuring the element temperature (for measuring the internal resistance) of the sensor element is applied to the sensor element 20 via a switching element 13 and a reference resistance R0.

Therefore, if the switching element 13 is turned ON during element temperature measurement, the voltage for measuring the element temperature is superimposed on the output Vs of the sensor element 11.

A battery voltage VB is applied to the heater 21, and a switching element 14 is disposed in a power supply circuit.

A CPU 15 within the control unit 4 reads the output Vs of the sensor element 20 via a filter (smoothing circuit) 16 and an A/D converter 17, at a predetermined timing, while controlling the ON/OFF of the switching element 13 for applying voltage used for measuring the element temperature.

Moreover, the CPU 15 performs a duty-control of the ON/OFF of the switching element 14 for controlling the heater via a D/A converter 18, to thereby control the power supply amount to the heater 21.

Next, the contents of control of the CPU 15 will be explained with reference to a flowchart.

Figure 5:
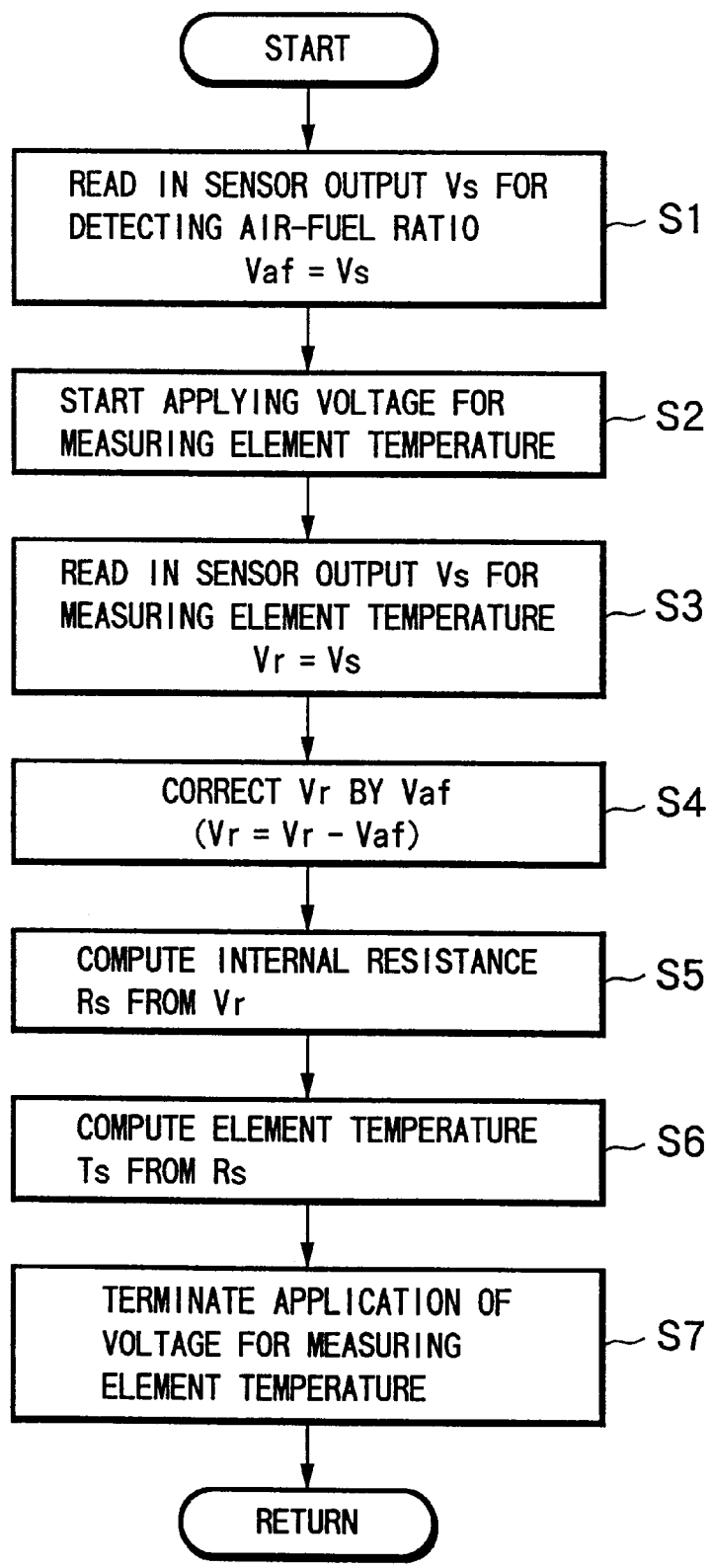
FIG. 5 is a flowchart showing the element temperature measurement routine (a first embodiment)

FIG. 5 is a flowchart showing the routine for measuring the element temperature according to a first embodiment, to be executed at a predetermined crank angle cycle.

In step 1 (abbreviated as "S1" in the drawing, the same holds hereinafter), the sensor output Vs is read in and set to Vaf=Vs, based on which the air-fuel ratio λ is detected.

In step 2, the switching element 13 is turned ON, and the application of voltage Vcc for measuring the element temperature to the sensor element 20 is started. In other words, immediately after reading the sensor output for air-fuel ratio detection, the application of voltage Vcc for measuring the element temperature is started.

In step 3, after a first predetermined time T1 has passed from the starting of application of voltage for measuring the element temperature, the sensor output Vs is read in and set to Vr=Vs so as to measure the internal resistance of the sensor element 20.

In step 4, the sensor output Vr being applied with voltage is corrected by the sensor output Vaf just before applied with voltage. Specifically, the sensor output Vaf just before applied with voltage is subtracted from the sensor output Vr being applied with voltage, to thereby obtain a corrected sensor output Vr=Vr−Vaf.

In step 5, the internal resistance Rs of the sensor element 20 is computed based on the corrected sensor output Vr.

Specifically, when the current flowing through sensor element 20 is i, and Vs=Vr, $$Vr = i \times Rs$$

$$Vcc - Vr = i \times R0.$$

Therefore, based on the above equations, the internal resistance Rs can be computed by $$Rs = Vr/[(Vcc - Vr)/R0]$$

In step 6, based on the internal resistance Rs of the sensor element 20, the element temperature Ts is computed for example by referring to a table. As the element temperature Ts becomes higher, the internal resistance Rs decreases, so the element temperature Ts can be computed from the internal resistance Rs.

In step 7, the switching element 13 is turned OFF after a second predetermined time T2 has passed from the starting of application of voltage for measuring the element temperature, to thereby stop (terminate) the application of voltage Vcc for measuring the element temperature to the sensor element 11.

Figure 6:
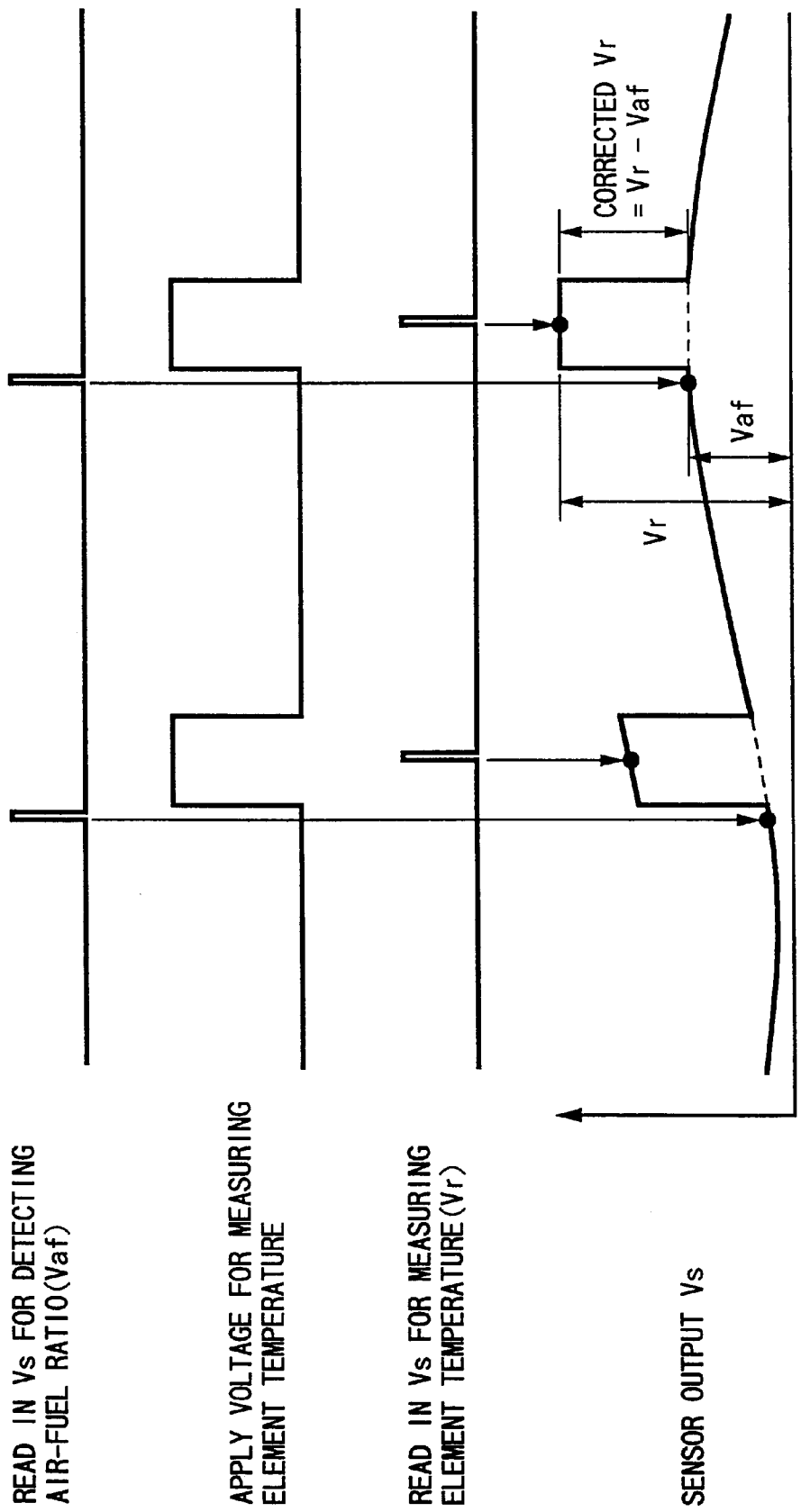
FIG. 6 is a time chart of the element temperature measurement.

Effects of the above-mentioned element temperature measurement will be explained with reference to FIG. 6.

In a case where the element temperature measurement voltage is applied to the sensor element of the air-fuel ratio sensor, since the sensor output is superimposed with an output signal equivalent to the oxygen battery of the sensor element, it is likely that the sensor output being applied with voltage is varied even if the element temperature is constant, thereby causing an error in estimating the element temperature.

Therefore, by correcting the sensor output Vr being applied with voltage by the sensor output Vaf just before applied with voltage, to be specific, by setting the corrected sensor output Vr to Vr=Vr−Vaf, an influence of the oxygen battery is eliminated, so that the internal resistance Rs is correctly computed based on the corrected sensor output Vr, and the estimation error of the element temperature Ts is eliminated.

Moreover, when detecting the air-fuel ratio by reading the sensor output at a predetermined crank angle cycle, the voltage for measuring the element temperature is applied to the sensor element immediately after reading the sensor output for air-fuel ratio detection. This enables to minimize the number of times in which, since the voltage is being applied, the air-fuel ratio is unable to be detected at air-fuel ratio detection timings during high speed rotation and the like, and it further enables to minimize the influence to the air-fuel ratio control performance. Also, the sensor output for air-fuel ratio detection can be read instead of sensor output just before applied with voltage.

Figure 7:
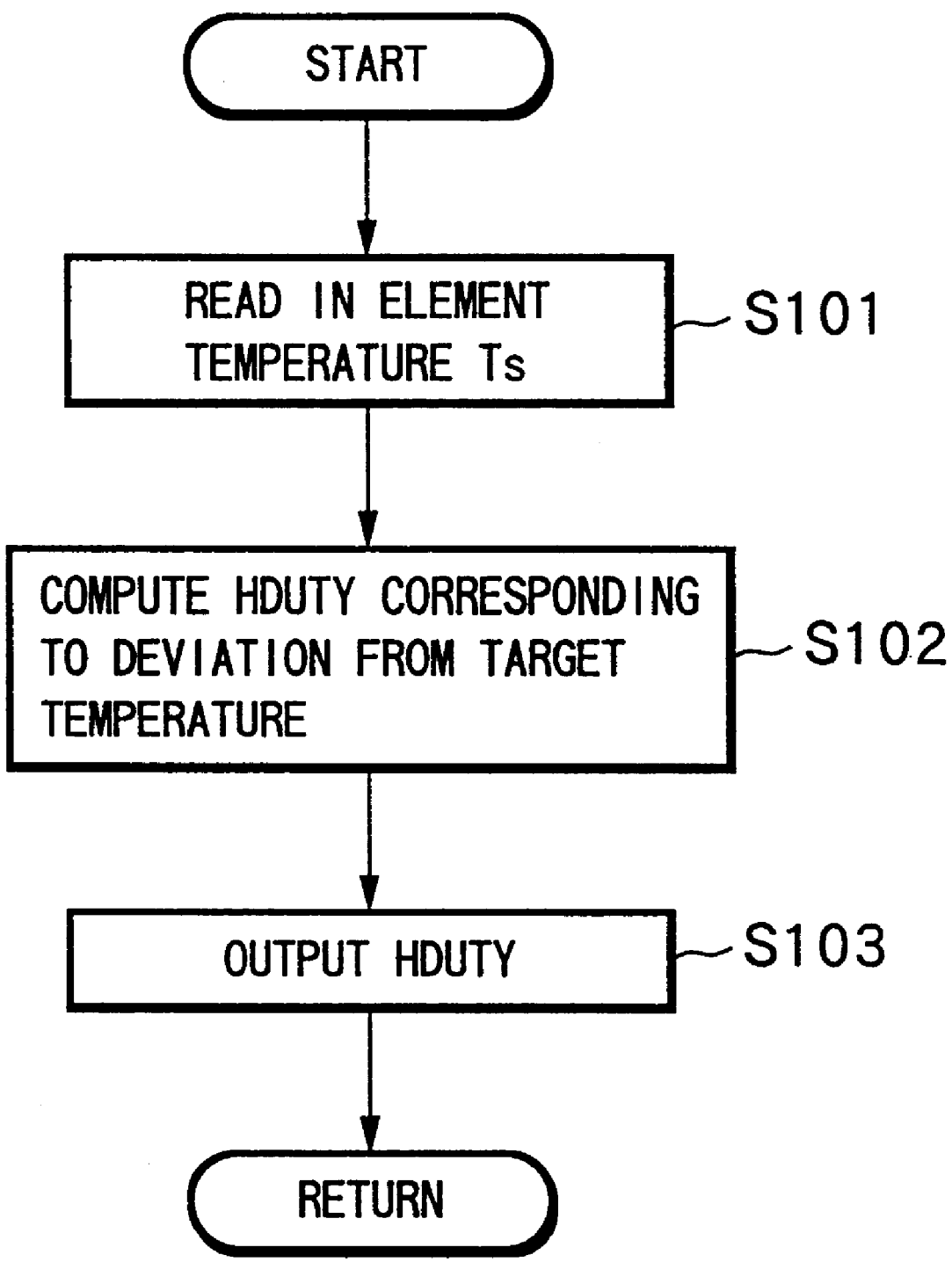
FIG. 7 is a flowchart showing the heater control routine.

FIG. 7 is a flowchart of the heater control routine, to be executed at each predetermined time.

In step 101, the latest element temperature Ts computed by the routine of FIG. 5 is read in.

In step 102, in accordance with a deviation between the actual element temperature Ts and the target temperature, a heater duty HDUTY (%) is computed using a known PID control, so as to approximate the element temperature Ts to the target temperature.

To be specific, when the actual element temperature Ts is lower than the target temperature, the heater duty HDUTY is increased so as to increase the power supply amount (power supply time ratio) to the heater 21. In contrast, when the actual element temperature Ts is higher than the target temperature, the heater duty HDUTY is decreased so as to reduce the power supply amount (power supply time ratio) to the heater 21.

In step 103, the computed heater duty HDUTY is output, whereby the switching element 14 is switched ON or OFF to control the power supply amount to the heater 12, thereby converging the element temperature Ts to the target temperature.

Incidentally, in the above embodiment, the internal resistance Rs of the sensor element 20 is measured, based on which the element temperature Ts is computed, thereby feedback controlling the element temperature Ts to reach the target temperature during heater control. However, since the element temperature Ts is determined based on the internal resistance Rs, the internal resistance Rs may be feedback controlled to reach the target internal resistance during heater control without computing the element temperature Ts.

In this case, when the actual internal resistance Rs is greater than the target internal resistance, the element temperature is low, so the heater duty HDUTY is increased so as to increase the power supply amount to the heater 21. In contrast, when the actual internal resistance Rs is smaller than the target internal resistance, the element temperature is high, so the heater duty HDUTY is decreased so as to reduce the power supply amount to the heater 21.

Next, other embodiments according to the present invention will be explained.

Figure 8:
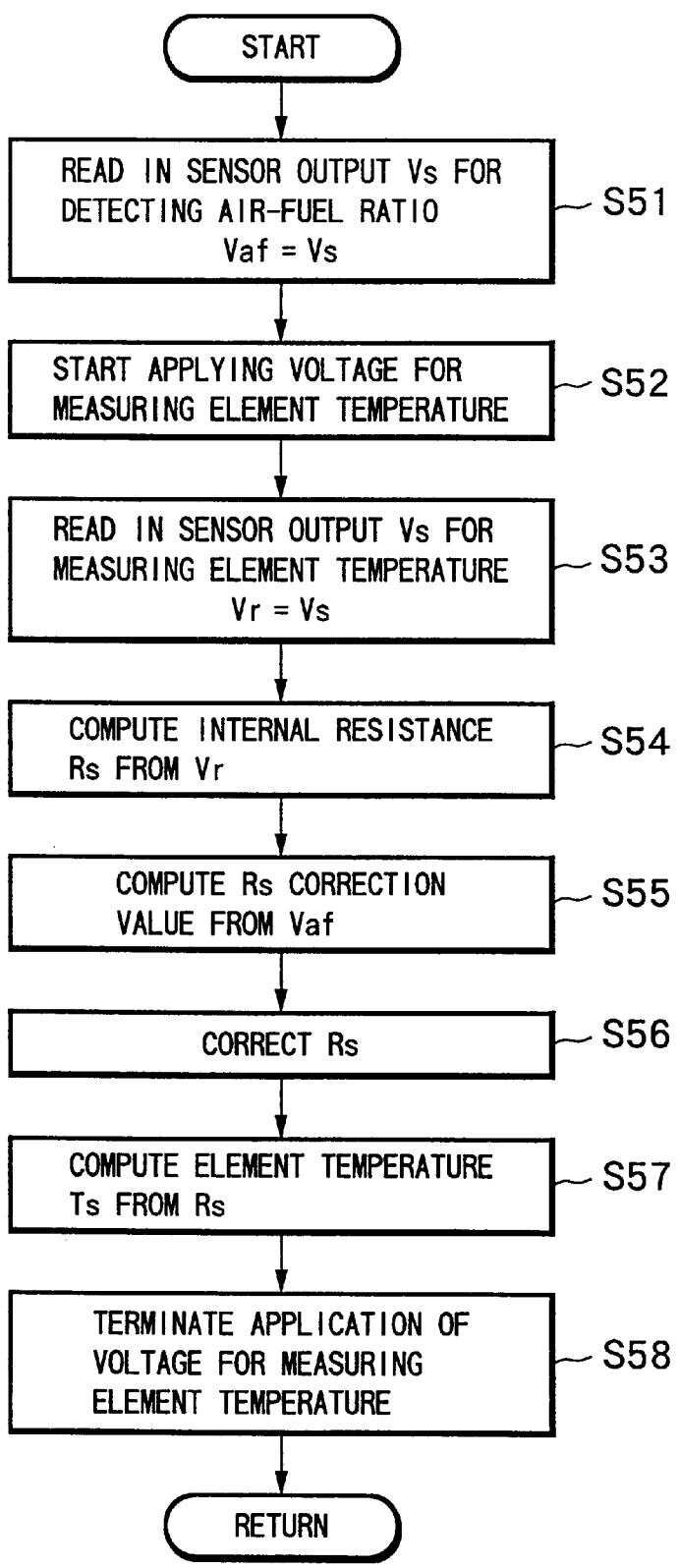
FIG. 8 is a flowchart showing the element temperature measurement routine according to a second embodiment.

FIG. 8 is a flowchart of the element temperature measurement routine according to a second embodiment, to be executed instead of the flowchart of FIG. 5.

Steps 51 through 53 are the same as steps 1 through 3 in the flowchart of FIG. 5.

In step 54, the internal resistance Rs of the sensor element 11 is computed based on the sensor output Vr being applied with voltage without correction.

In step 55, the correction value for the internal resistance Rs (Rs correction value) is computed from the sensor output Vaf just before applied with voltage.

In step 56, the internal resistance Rs computed in step 54 is corrected by the Rs correction value computed in step 55.

The correction here is performed so that when the sensor output Vaf just before applied with voltage is greater, the internal resistance Rs is corrected to a smaller value, since when the sensor output Vaf just before applied with voltage is greater, the internal resistance Rs is computed to be greater than the actual value.

Then, in step 57, the element temperature Ts is computed based on the internal resistance Rs (corrected Rs) of the sensor element 11 by referring to a table and the like. Step 58 is the same as step 7 in the flowchart of FIG. 5.

Figure 9:
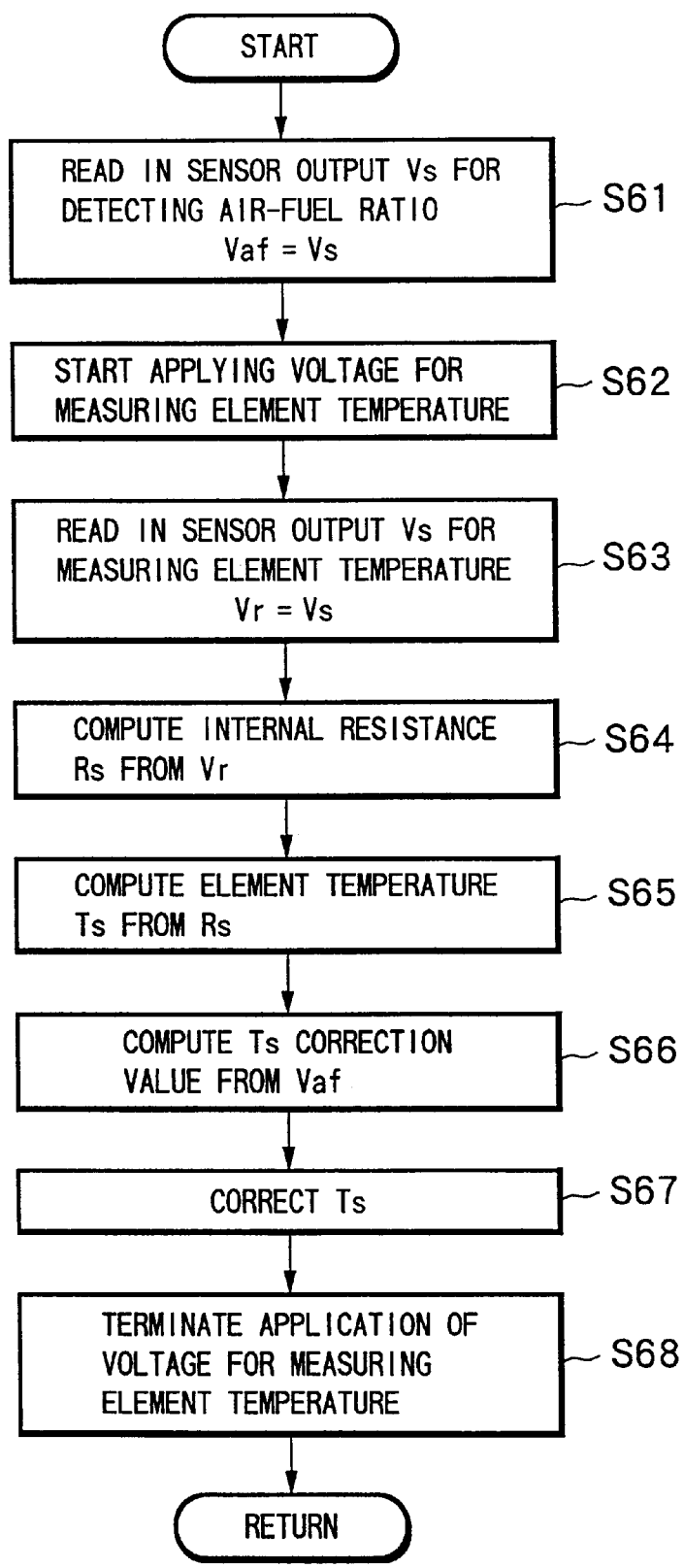
FIG. 9 is a flowchart showing the element temperature measurement routine according to a third embodiment.

FIG. 9 is a flowchart showing the element temperature measurement routine according to a third embodiment, to be executed instead of the flowchart of FIG. 5.

Steps 61 through 63 are the same as steps 1 through 3 in the flowchart of FIG. 5.

In step 64, the internal resistance Rs of the sensor element 20 is computed based on the sensor output Vr being applied with voltage without correction. In step 65, the element temperature Ts is computed based on the internal resistance Rs of the sensor element 20 by referring to a table and the like.

In step 66, the correction value for element temperature Ts (Ts correction value) is computed based on the sensor output Vaf just before applied with voltage.

In step 67, the element temperature Ts computed in step 64 is corrected by the Ts correction value computed in step 66.

The correction here is performed so that when the sensor output Vaf just before applied with voltage is greater, the internal resistance Rs is corrected to a smaller value, since when the sensor output Vaf just before applied with voltage is greater, the internal resistance Rs is computed to be greater than the actual value and the element temperature Ts is therefore computed to be lower than the actual temperature. Accordingly, the corrected element temperature Ts (corrected Ts) is used for controlling the heater and the like. Step 68 is the same as step 7 in the flowchart of FIG. 5.

Next, an explanation will be made for where the impedance of the sensor element of the air-fuel ratio sensor 8 is measured, and the element temperature is measured based on the measured impedance.

Figure 10:
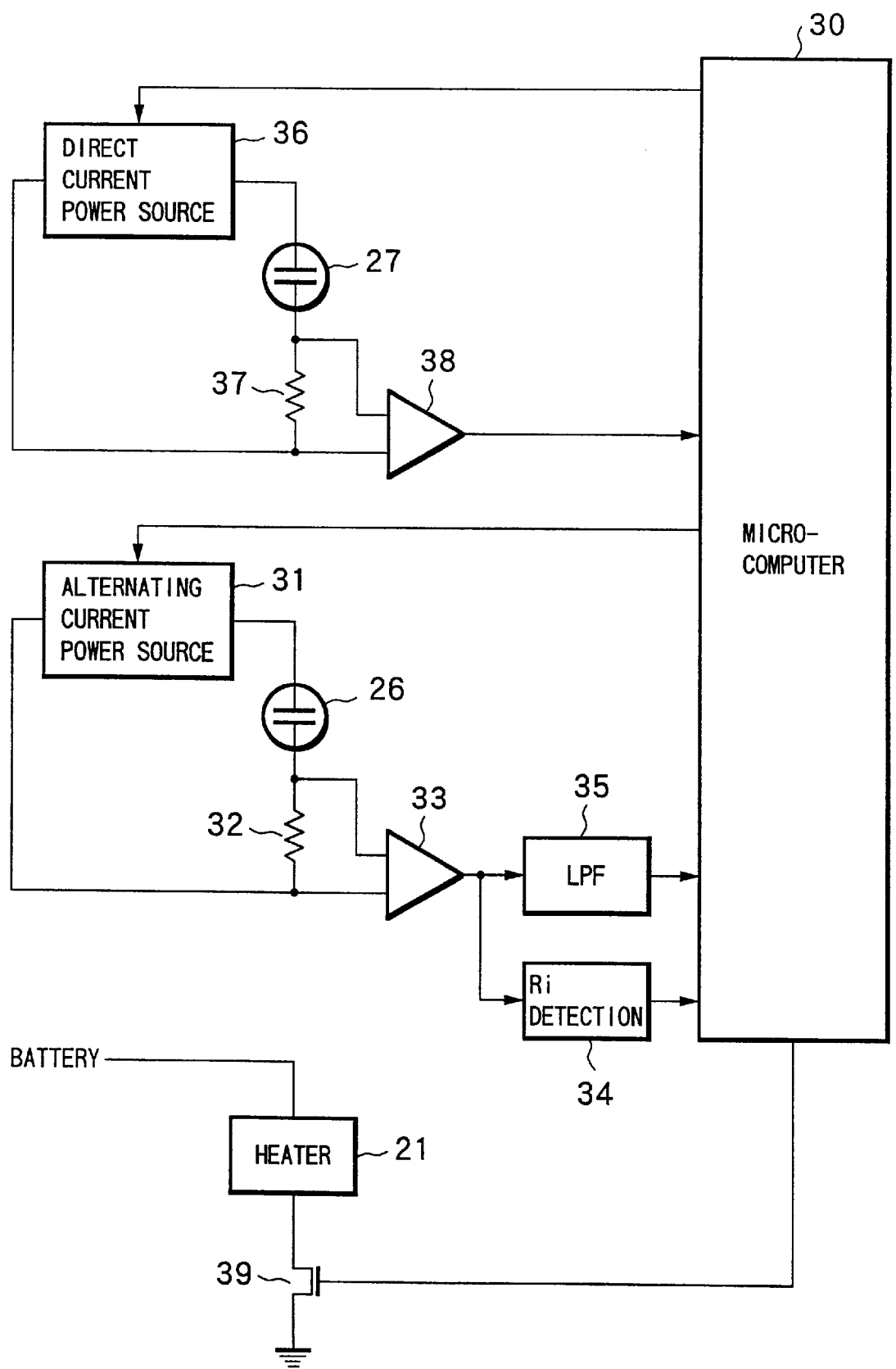
FIG. 10 is a second control circuit diagram for the heater and the sensor element of the air-fuel ratio sensor.

FIG. 10 shows a second control circuit for the sensor element portion 20 of the air-fuel ratio sensor (Nernst cell portion 26, pump cell portion 27) and the heater 21 for heating the sensor element.

In the present control circuit, under the control of a microcomputer 30, an alternating voltage is applied from an AC power source 31 to the Nernst cell portion 26 for measuring impedance, and the current value Is flowing through the Nernst cell portion 26 is voltage converted and detected by a current detecting resister 32 and a detecting amplifier 33.

A signal from the detecting amplifier 33 is input for example to an impedance detecting circuit 34 comprising a high pass filter and an integrator, so that only an alternating current component is taken out to detect the impedance Ri from the amplitude of the alternating component. Thereby, the impedance Ri of the Nernst cell portion 26 can be measured.

Moreover, the signal from the detecting amplifier 33 is input to a low pass filter 35, so that only a direct current component is taken out to detect a voltage generated at the Nernst cell portion 26 corresponding to the oxygen concentration. Thereby, the lean/rich of oxygen concentration can be detected.

Under the control of the microcomputer 30, a predetermined voltage Vp is applied by a DC power source 36 to the pump cell portion 27, but the direction of application is inverted corresponding to the rich/lean of the oxygen concentration detected by the Nernst cell portion 26, so that the current value Ip flowing through the pump cell portion 27 is voltage converted and detected by a current detecting resister 37 and a detecting amplifier 38. Thereby, the air-fuel ratio λ is detected.

A battery is used to apply a battery voltage VB to the heater 21, but since a switching element 39 is disposed in a power supply circuit similar to the first control circuit (FIG. 4), normally the microcomputer 30 performs a duty-control of the ON/OFF of the switching element 39, thereby enabling the control of the power supply amount to the heater 21.

Figure 11:
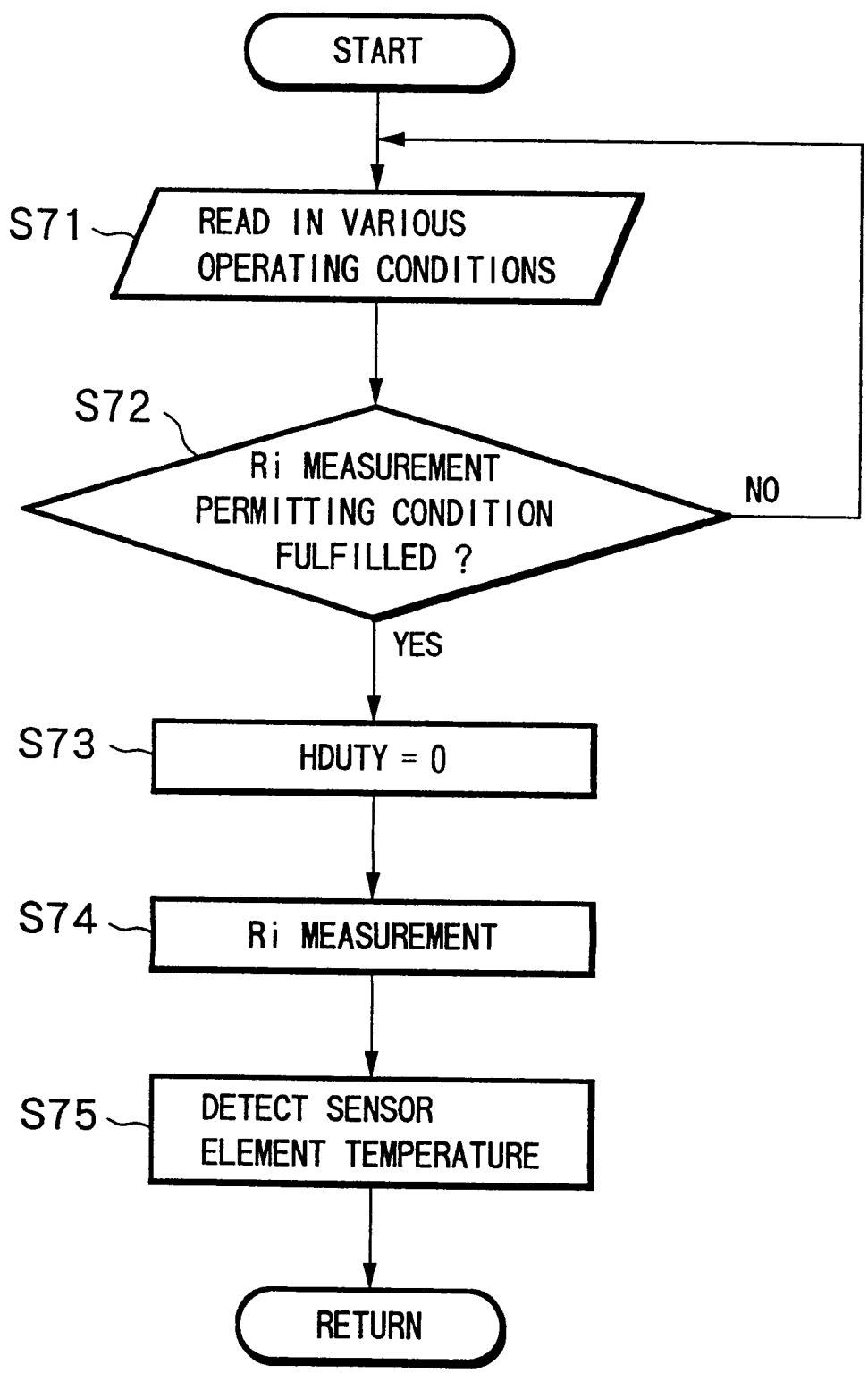
FIG. 11 is a flowchart showing the element temperature measurement routine according to a fourth embodiment.

FIG. 11 is a flowchart showing the element temperature measurement routine according to a fourth embodiment, to be executed at each predetermined time by the microcomputer 30.

In step 71, various operating conditions are read in.

In step 72, it is judged whether or not an impedance Ri measurement permitting condition is fulfilled. Here, the impedance Ri measurement permitting condition is fulfilled when an influence of heat-draw (?) caused by a change in exhaust flow rate is small, for example, when the operating condition of the engine is within a predetermined rotation speed Ne and a predetermined fuel injection quantity Tp.

When the impedance measurement permitting condition is not fulfilled, the procedure returns to step 71.

When the impedance measurement permitting condition is fulfilled, the procedure advances to step 73, where the heater duty (HDUTY) is set to 0 (%), and after stopping the power supply to the heater 21, the procedure advances to step 74.

In step 74, the impedance of the sensor element (Nernst cell portion 26) is measured. Specifically, a predetermined alternating voltage is applied to the Nernst cell portion 26 from the AC power source 31, and a terminal voltage of the current detecting resister 32 at that time is read in, based on which the impedance Ri of the Nernst cell portion 26 is measured.

Figure 12A:
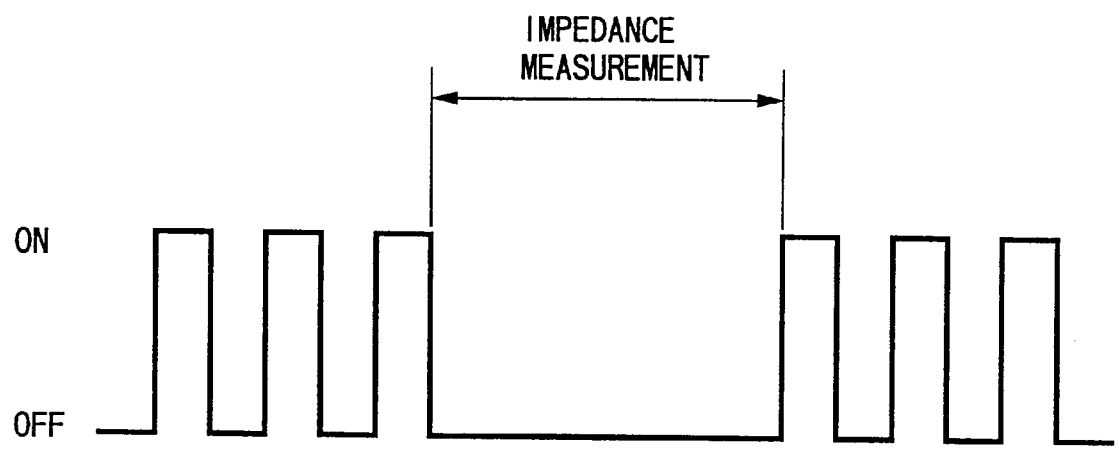
FIGS. 12(a) and 12(b) is a diagram showing the duty control (ON/OFF state) during impedance measurement.

That is, as shown in FIG. 12A, during measurement of impedance Ri, the power supply to the heater for heating the sensor element is turned OFF (applied voltage: 0V) and this state is maintained.

Thereafter, the procedure advances to step 75, where the element temperature is detected based on the impedance Ri measured in step 74, by searching a table and the like set in advance of the element temperature and a theoretical value of impedance Ri.

After terminating the above impedance measurement, a normal duty control is resumed by the power supply to the heater 21.

Based on the above routine, the power supply to the heater for heating the sensor element is stopped (maintaining the applied voltage to be constant as 0V) during impedance measurement of the sensor element so that the impedance can be measured at the element temperature approximately equal to the exhaust temperature at that time while preventing the momentary fluctuation of the sensor element temperature. Thereby, the impedance measurement accuracy of the sensor element is improved, and further, the detection accuracy of the sensor element temperature is improved.

Figure 12B:
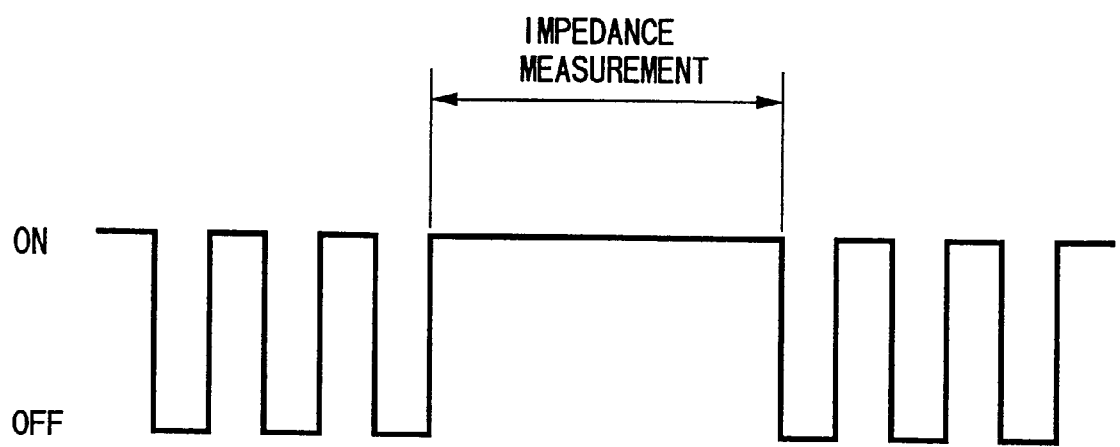

Moreover, in step 73 of the flowchart of FIG. 11, during impedance measurement of the sensor element, the heater duty (HDUTY) may be set to 100 (%), to turn the power supply to the heater ON and to maintain this state, as shown in FIG. 12B. Therefore, the applied voltage can be maintained to be constant as the maximum set value and the momentary fluctuation of the sensor element temperature is prevented, to thereby enable the impedance measurement in a stable state.

The voltage during impedance measurement may be set in advance by resistance adjustment and the like without performing the above-mentioned duty control. A control circuit for controlling the heater for the sensor element in such a case is shown in FIG. 13.

Figure 13A:
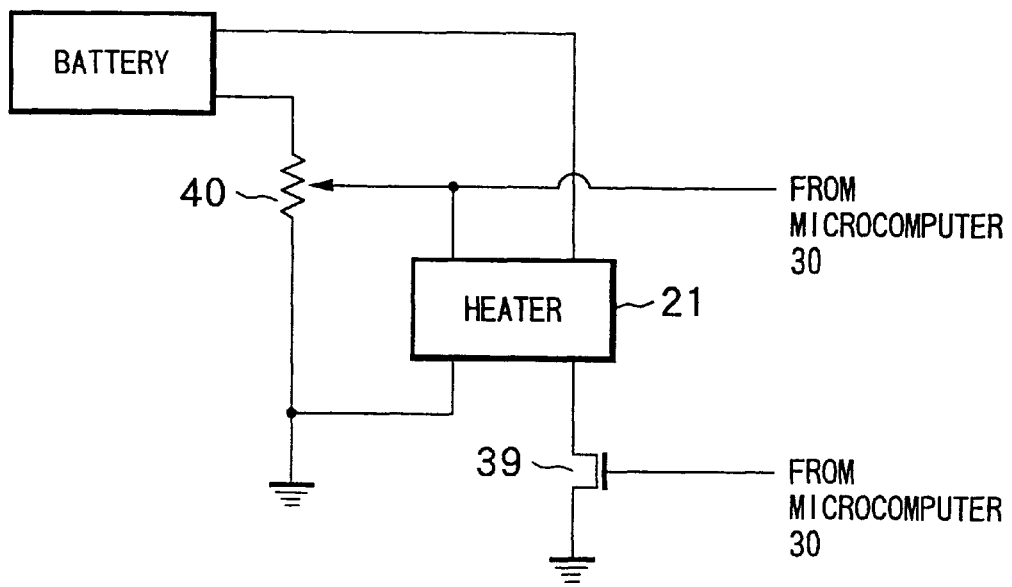
FIGS. 13(a) and 13(b) shows another control circuit diagram for the heater of the air-fuel ratio sensor.

As shown in FIG. 13A, the present control circuit is constituted to control the power supply amount of the heater 21 by performing the duty-control of the ON/OFF of the switching element 39 by the microcomputer 30 in a normal state, similar to the above-mentioned embodiment, whereas during impedance measurement, to select a voltage value set in advance by resistance adjustment of a switch 40 for application to the heater 21.

Figure 13B:
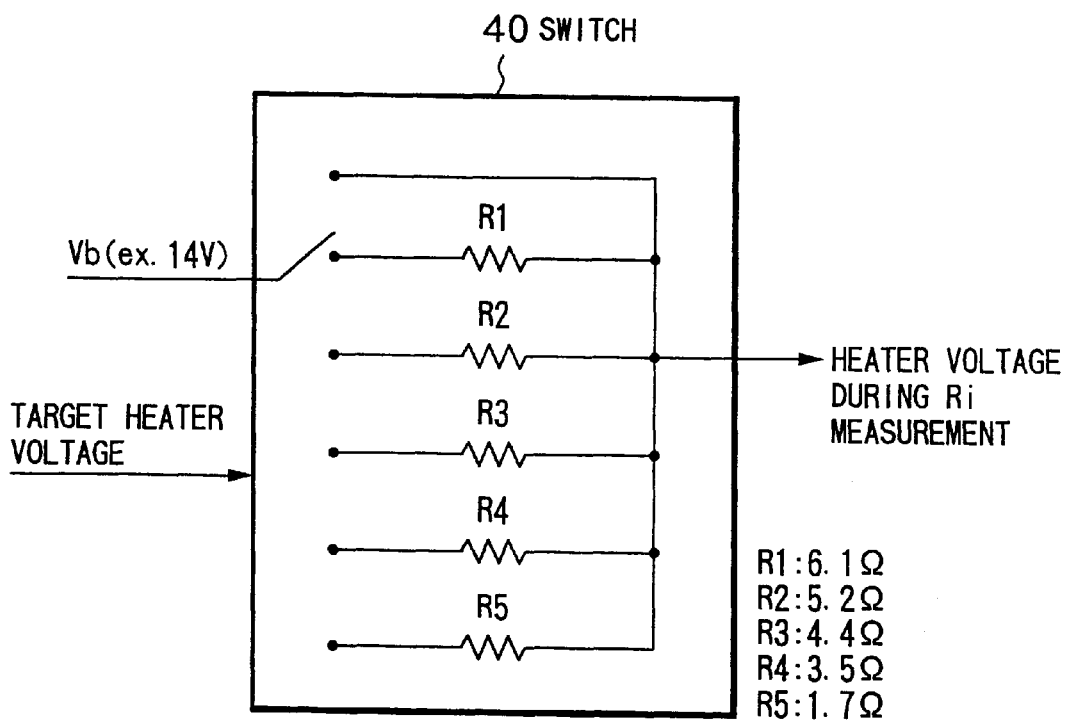

The switch 40 sets an applied voltage value for the heater for example by arbitrarily selecting a plurality of resistances as shown in FIG. 13B.

Figure 14:
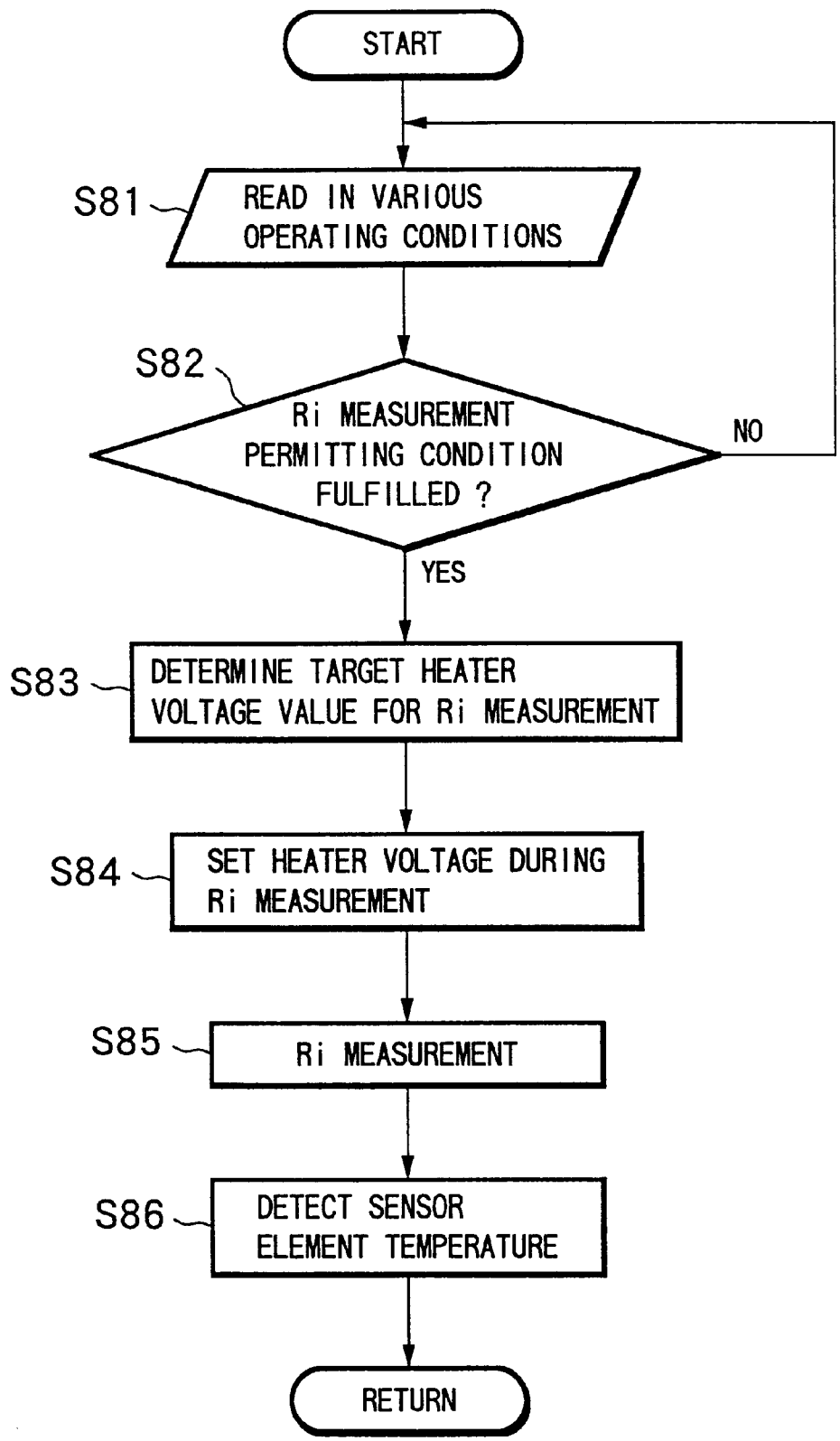
FIG. 14 is a flowchart showing the element temperature measurement routine according to a fifth embodiment.

FIG. 14 is a flowchart of the element temperature measurement routine according to a fifth embodiment.

Steps 81 and 82 are the same as steps 71 and 72 in the flowchart of FIG. 11, so explanations thereof are omitted.

When the impedance Ri measurement permitting condition is fulfilled in step 82, the procedure advances to step 83.

In step 83, the target heater voltage during impedance measurement is determined by searching through a map and the like set in advance based on the read engine rotation speed Ne and fuel injection quantity Tp. Thereby, the applied voltage can be set corresponding to the exhaust temperature approximately equal to the element temperature, to prevent the fluctuation of element temperature.

Next, in step 84, the resistance of the switch 40 is adjusted so as to set the hater voltage to the target heater voltage determined in step 83. Then, the procedure advances to step 85, where the impedance Ri is measured.

Then, the procedure advances to step 86 where the table and the like set in advance of the element temperature and the theoretical value of impedance Ri are searched, to detect the element temperature based on the impedance Ri measured in step 85.

From the above, during impedance measurement, the voltage set based on the engine rotation speed Ne and the fuel injection quantity Tp is applied to the heater, thereby preventing the fluctuation of element temperature and also minimizing the variation of element temperature before and after impedance measurement, thereby enabling even more accurate impedance measurement.

Further, the present invention is not limited to the above embodiments where the heater control is performed by a duty control (in a normal state), but can achieve the same advantageous effects even in a case where the heater control is performed by any other control method, such as a method of controlling the applied voltage to the heater.

The entire contents of Japanese Patent Application No. 2000-144427, filed May 17, 2000, and Japanese Patent Application No. 2000-197020, filed Jun. 29, 2000, are herein incorporated by reference.

What is claimed:

1. A device for measuring element temperature of an air-fuel ratio sensor comprising:

a heater for heating a sensor element of said air-fuel ratio sensor equipped to an exhaust system of an internal combustion engine;

an internal resistance measurement circuit for measuring internal resistance of said sensor element;

an arithmetic circuit for computing the element temperature based on said measured internal resistance, and computing a power supply amount to said heater for heating the sensor element based on said computed element temperature;

a heater control circuit for controlling said heater based on said computed power supply amount; and a heater applied voltage control circuit for maintaining a heater applied voltage to said heater for heating the sensor element to be constant during internal resistance measurement of the sensor element.

2. The device according to claim 1, wherein said air-fuel ratio sensor is equipped with a Nernst cell portion for generating an element voltage corresponding to lean/rich of an air-fuel ratio, and a pump cell portion for being applied with a predetermined pump voltage in a direction corresponding to the lean/rich of the air-fuel ratio detected by said Nernst cell portion, to continuously vary a current value thereof corresponding to the air-fuel ratio; and wherein said internal resistance measurement circuit measures internal resistance of said Nernst cell portion based on a current value flowing through said Nernst cell portion when an alternating voltage for internal resistance measurement is applied to said Nernst cell portion.

3. The device according to claim 1, wherein said heater control circuit controls the power supply amount to the heater by performing a duty control of the ON/OFF of the power supply to the heater; and wherein said heater applied voltage control circuit maintains the power supply to the heater to an OFF state during internal resistance measurement of said sensor element.

4. The device according to claim 1,
wherein said heater control circuit controls the power supply amount to the heater by performing a duty control of ON/OFF of the power supply to the heater; and
wherein said heater applied voltage control circuit maintains the power supply to the heater to an ON state during internal resistance measurement of said sensor element.

5. A device for measuring element temperature of an air-fuel ratio sensor comprising:
a heater for heating a sensor element of said air-fuel ratio sensor equipped to an exhaust system of an internal combustion engine;
internal resistance measurement means for measuring internal resistance of said sensor element;
heater power supply amount computing means for detecting the sensor element temperature based on said measured internal resistance, to compute a power supply amount to said heater for heating the sensor element based on said detected element temperature;
heater control means for controlling said heater based on said computed heater power supply amount; and
heater applied voltage control means for maintaining a heater applied voltage to said heater for heating the sensor element to be constant during internal resistance measurement of the sensor element.

6. A method for measuring element temperature of an air-fuel ratio sensor comprising the steps of:
measuring internal resistance of a sensor element of said air-fuel ratio sensor equipped to an exhaust system of an internal combustion engine, computing the element temperature based on said measured internal resistance, and computing a power supply amount to a heater for heating the sensor element based on said computed element temperature; and
maintaining a heater applied voltage to said heater for heating the sensor element to be constant during internal resistance measurement of the sensor element.

7. The method according to claim 6,
wherein said air-fuel ratio sensor is equipped with a Nernst cell portion for generating an element voltage corresponding to lean/rich of an air-fuel ratio, and a pump cell portion for being applied with a predetermined pump voltage in a direction corresponding to the lean/rich of the air-fuel ratio detected by said Nernst cell portion, to continuously vary a current value thereof corresponding to the air-fuel ratio; and
wherein internal resistance of said Nernst cell portion is measured based on a current value flowing through said Nernst cell portion when an alternating voltage for internal resistance measurement is applied to said Nernst cell portion.

8. The method according to claim 6,
wherein the power supply amount to the heater for heating the sensor element is controlled by performing a duty control of ON/OFF of the power supply to the heater; and
wherein the power supply to the heater is maintained to an OFF state during internal resistance measurement of said sensor element.

9. The method according to claim 6,
wherein the power supply amount to the heater for heating the sensor element is controlled by performing a duty control of ON/OFF of the power supply to the heater; and
wherein the power supply to the heater is maintained to an ON state during internal resistance measurement of said sensor element.

* * * * *